(12) United States Patent
Tsukada

(10) Patent No.: US 6,831,735 B2
(45) Date of Patent: Dec. 14, 2004

(54) ANALYTICAL METHOD AND DEVICE USING DISC CYTOMETRY

(75) Inventor: Mamoru Tsukada, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/118,936

(22) Filed: Apr. 10, 2002

(65) Prior Publication Data

US 2002/0149763 A1 Oct. 17, 2002

(30) Foreign Application Priority Data

Apr. 11, 2001 (JP) .......................... 2001-112612

(51) Int. Cl.[7] .................. G01N 21/00; G01N 15/02; G01N 33/48; G01N 15/06; C12Q 1/02
(52) U.S. Cl. .................. 356/73; 356/336; 356/337; 356/342; 356/343; 436/63; 435/29; 210/781; 422/100; 422/102; 250/574
(58) Field of Search .................. 356/73, 336, 337, 356/342, 343; 436/63; 435/29; 210/781, 745, 739; 422/100, 102; 250/574, 214 C

(56) References Cited

U.S. PATENT DOCUMENTS

| | | | | |
|---|---|---|---|---|
| 4,765,737 A | * | 8/1988 | Harris et al. | |
| 5,104,221 A | * | 4/1992 | Bott et al. | |
| 5,325,168 A | * | 6/1994 | Nakamoto et al. | |
| 5,525,240 A | * | 6/1996 | Lemelson | 210/745 |
| 5,540,494 A | * | 7/1996 | Purvis | |
| 6,245,572 B1 | * | 6/2001 | Wall | |
| 6,254,834 B1 | * | 7/2001 | Anderson et al. | |
| 6,479,239 B1 | * | 11/2002 | Anderson et al. | |
| 6,534,262 B1 | * | 3/2003 | McKernan et al. | 435/6 |

* cited by examiner

Primary Examiner—Gregory J. Toatley, Jr.
Assistant Examiner—Khaled Brown
(74) Attorney, Agent, or Firm—Fitzpatrick, Cella, Harper & Scinto

(57) ABSTRACT

The analytical method having both flow cytometery and cytodiagnosis functions comprises the steps of: preparing a sample containing particulate substances such as cells and viruses; injecting the sample into a plate-like sample container; centrifuging the sample container; and using the sample container in which a distribution of the particulate substances has been formed as a preparation for analysis. The preparation is scanned with a laser beam to obtain analytical data. An analytical device for this method is also provided.

11 Claims, 4 Drawing Sheets

ANALYTICAL METHOD AND DEVICE USING DISC CYTOMETRY

BACKGROUND OF THE INVENTION

1. Field of the Invention

The present invention relates to a novel analytical method and device for analyzing cells, DNA, antigens and viruses in the field of laboratory tests such as a clinical examination. In particular, the invention relates to a novel, analytical method and device to combine cytometry and cytodiagnosis.

2. Related Background Art

A flow cytometer is a popular analytical device for flow cytometry. Flow cytometry is an analytical method where a cellular surface antigen is stained with one or more fluorescence-labeled specific antibodies, or DNA is stained with various dyes that bind to DNA, and obtained parameters, i.e., intensities of fluorescence, respective intensities of forward and side-way scattering light, and the individual numbers, are subjected to various analyses. On the other hand, in the fields of pathology, cytodiagnosis and hemodiagnosis, usually chemically stained smears are prepared and judged on a microscopic level.

In clinical cytodiagnosis, final judgment by an expert is still required in many cases, no matter how instruments have been automated and techniques for judging with image processing have been advanced. On the other hand, in flow cytometry, image observation is not involved. Thus, although flow cytometry has been recognized as a superior clinical test method because of its operability and simplicity, valuable information may be wasted. Under such circumstances, Japanese Patent Application Laid-Open No. 5-119035 ("Imaging Flow Cytometer") disclosed a flow cytometer having an image-pick up function. However, this device cannot provide specimens, because cells flow out from the flow cell.

SUMMARY OF THE INVENTION

Accordingly, an object of the invention is to provide a novel analytical device that can function to both prepare a specimen required for current cytodiagnosis and as a flow cytometer, and provide a novel, analytical method of flow cytometry with specimen preparation.

In order to overcome the above-described problem, the inventor conducted an intensive investigation and has finally invented a novel, analytical method and device, which have both an imaging function and specimen-preparation function by combining a centrifugation method and a fluorescence-labeling technique, such as flow cytometry. This analytical device is, so to speak, a flow cytometer having imaging and specimen-preparing functions. Here, this analytical device is referred to as a disc cytometer, because it typically uses a disc-shaped sample container, and the method is referred to as flow cytometry. It should be understood, however, that the shape of the sample container is not limited to a disc, as will be evident from the following description. The sample container must be made up of an optically transparent material, because it is used for cytodiagnosis, immunofluorescence analysis, images of cells etc.

This disc cytometry adopts differential centrifugation or density-gradient centrifugation, which has been used for isolating and purifying biological materials. In density-gradient centrifugation, a sample in a centrifuge tube is spun, and substances in the sample are distributed along a density gradient according to the differences in size, shape, density or specific gravity. In this invention, a plate-shaped sample container is used, which enables in situ cytodiagnosis as well as analysis and imaging by the fluorescence-labeling method in one container, instead of a cylindrical centrifuging tube employed in conventional density-gradient centrifugation. The sample container is preferably in the form of a disc in view of centrifugation, but it can be in any form as long as it is suitable for centrifugation, for example, a rectangular sample container.

As the medium for generating a density gradient during centrifugation, PEG (polyethylene glycol) or sucrose in an appropriate range is used for biological samples. In clinical laboratory tests, commercial solutions such as Ficoll (trade name) and Percoll (trade name) may be used, depending on the purpose.

One aspect of the present invention is an analytical method comprising the steps of: preparing a sample containing particulate substances; injecting the sample into a plate-like sample container; centrifuging the sample container; and using the sample container in which a distribution of the particulate substances has been formed as a preparation for analysis.

The term "particulate substances", "cells", etc. as used herein refer to biological materials, which are subjected to cytodiagnosis or clinical laboratory test, for example, those selected from the group consisting of cells, microbial cells, viruses, DNA and mitochondria.

Further, in this invention, the sample container preparation is irradiated and scanned with a laser beam to obtain at least one set of analytical data selected from fluorescence intensity, scattered light intensity and light scattering particle number for particulate substances in the sample. The particulate substances may be subjected to a fluorescence labeling reaction before centrifugation. The image data of particulate substances may be obtained on the basis of analytical data.

In this invention, the same experimental protocols as used in conventional flow cytometry can be used for sample preparation and reaction with florescent antibodies. Accordingly, when a suitably reacted sample is introduced and overlayed on the density gradient solution in a disc container, and centrifuged for a predetermined time at a predetermined rotation speed, the cells, etc. are arranged along the formed density gradient. Then, a laser scan of the disc container is carried out in the radius direction with rotation of the container to obtain information such as fluorescence intensity, scattered light intensity and the individual number. Depending on the purpose, image information at a certain position of the disc container can be obtained by using positional information of the disc container from a sensor and an optical system of confocal laser microscope.

This is the disc-cytometry analysis of the present invention.

Another aspect of the present invention is an analytical device comprising: means for centrifuging a plate-like sample container; means for generating a laser beam; means for scanning the sample container and irradiating particulate substances having been centrifuged in the sample container with a laser beam; and means for detecting scattered light from the sample container.

In this invention, the means for detecting scattered light may be a means for detecting light scattered from the disc container at different angles. In such a case, preferably, the fluorescence intensities and/or the number of the particulate substances are detected based on the a plurality of scattered light. Preferably, the irradiating means scans the rotating disc container in a radius direction with a laser beam.

Further, the analytical device of this invention may be provided with a means for processing and analyzing data by A/D converting the signals from the scattered light detecting means and using the same as a parameter. In addition, it may be provided with an optical system and an image pick-up means for obtaining images of the particulate substances.

The specimen-providing function of the present invention is very useful for clinical judgement as a supplementary confirmation means. For example, it can be used for discrimination of leukemia from malignant lymphoma, acute lymphoblastic leukemia from acute crisis of chronic myelogenous leukemia, and lymphoblastic leukemia from non-lymphoblastic leukemia, all of which are considered to be difficult to discriminate only by current flow cytometry. Also, it can be used for identification of immature T cells and for identification of neoplasm, which is difficult to identify solely by the DNA Index.

DESCRIPTION OF THE PREFERRED EMBODIMENTS

In the following, preferred embodiments of this invention will be described with reference to the accompanied drawings. First referring to FIG. 1, there is shown a perspective view illustrating the principle of this invention.

Figure 1:
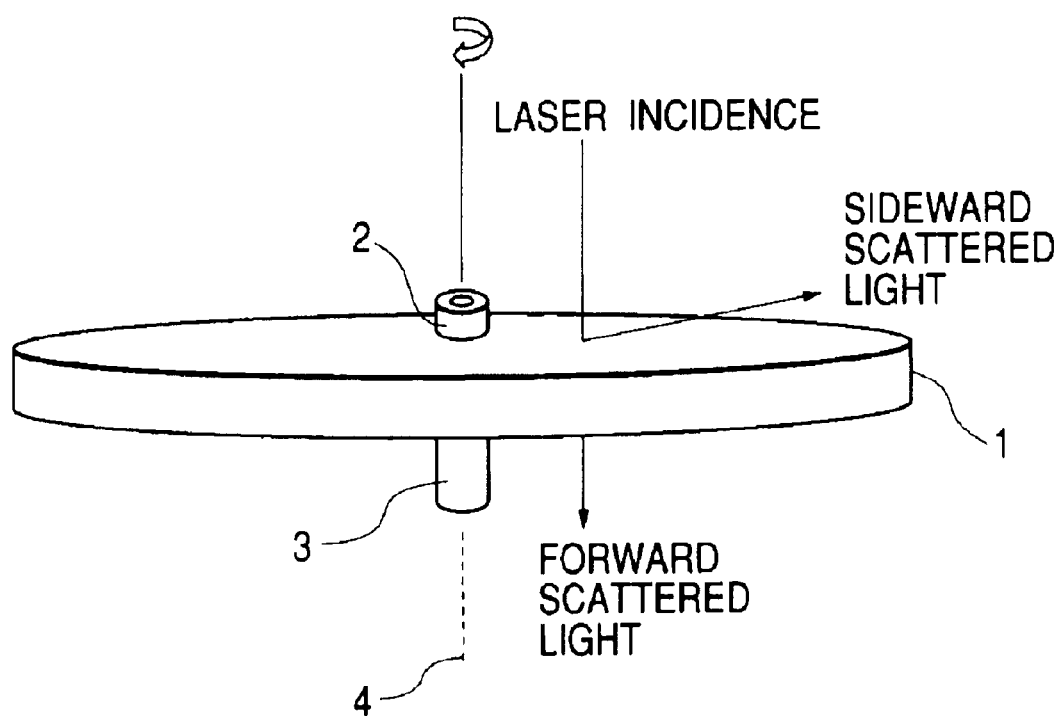
FIG. 1 is a perspective view illustrating the principle of the invention.

In FIG. 1, a transparent plate-like sample container is a disc sample container 1. The sample container 1 is, for example, 80 mm in radius and 1 mm in height as measured inside. The container is made of a poly(methyl methacrylate) (PMMA) resin, which is generally used for disposable sample cells, because of its uniform transmission properties with respect to visible light and light with wavelength of 280 to 360 nm. In the center of the upper surface of the sample container 1, a sample inlet 2 is provided, and in the center of the lower surface of the same, a sample outlet 3 is formed to face the sample inlet 2.

The sample container is filled with a gradient solution through the sample inlet 2, and then a sample solution containing cells, etc. is overlaid on the gradient solution, and the sample outlet 3 is capped with a screw cap. The sample solution has already been subjected to intended fluorescence-labeling. Then, the sample container 1 is rotated around an axis of rotation 4 for centrifugation. After the centrifugation, the entire sample container 1 is scanned with a laser beam to measure the intensities of the forward and sideward scattered light and the fluorescence labeling intensity. Further, the sample at a desired position within the sample container 1 is observed under a microscope or the image is picked up.

Figure 2:
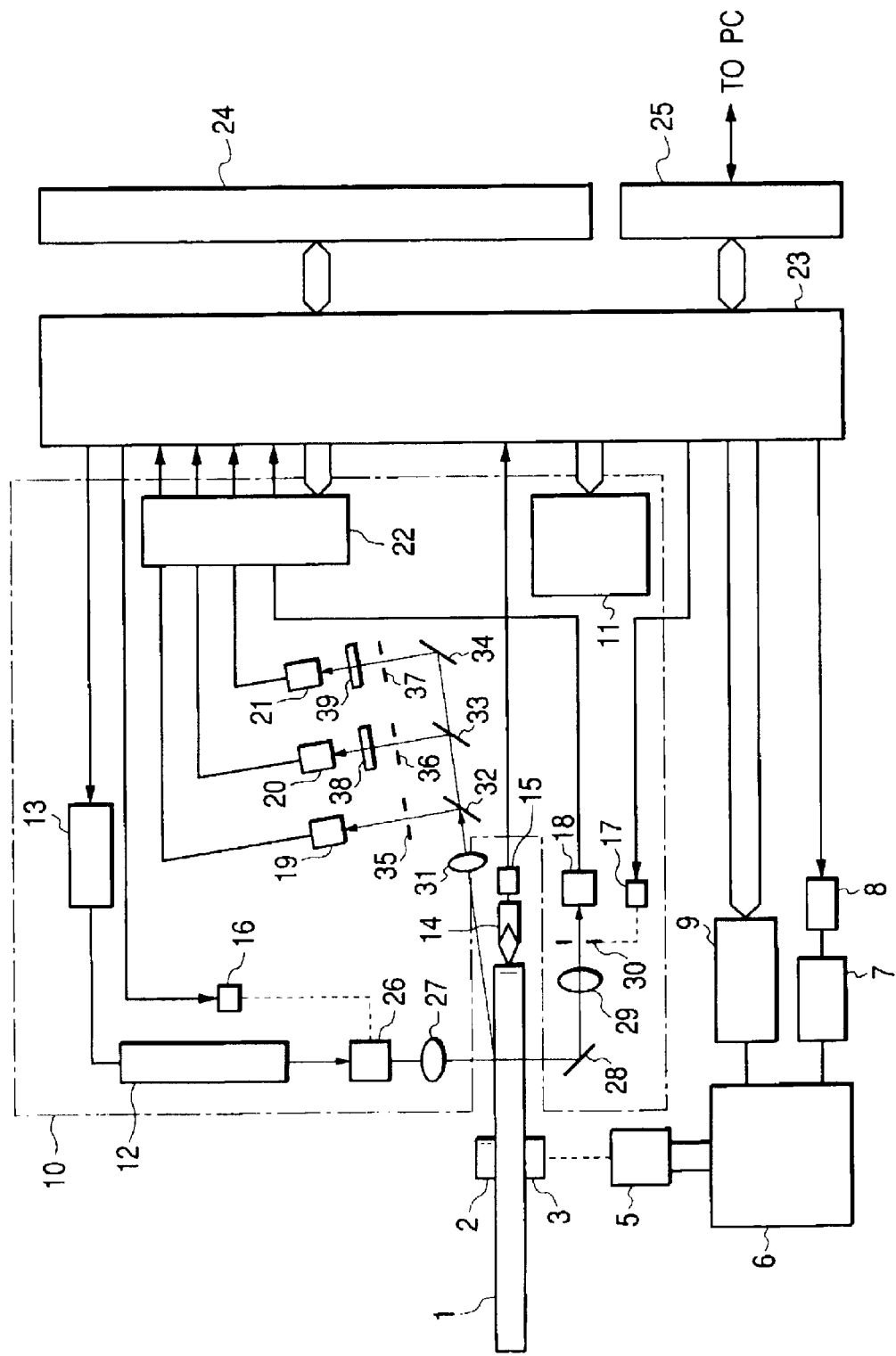
FIG. 2 is a block diagram illustrating the configuration of an analytical device of the embodiment of the invention.

FIG. 2 is a block diagram illustrating the structure of an analytical device according to one embodiment of the invention. This analytical device includes: a disc holder 5 for vacuum mounting a disc sample container 1 on the device; a motor 6 for rotating the disc holder 5; a pump 7 and an electromagnetic valve 8 for vacuum mounting of the sample container; a motor controller 9 for controlling the motor 6; a movable unit 10, which is described below; a reflection-type sensor 14 and a binarizing unit 15 for detecting the rotational angle of the sample container 1; a single chip microcomputer 23 for controlling the electromagnetic valve 8, the motor controller 9 and the movable unit 10 and receiving signals from the movable unit 10 and the binarizing unit 15; an external memory 24 connected to the single chip microcomputer 23; and a USB (universal serial bus) interface 25 for connecting an external personal computer (PC) and the single chip microcomputer 23 with each other. The mechanism of vacuum-mounting the disc-like sample container 1 on the device is, in principle, the same as a spin coater used in the semiconductor device manufacturing process, and the sample container is vacuum-mounted on the device by evacuating the air in the holder with the pump 7. Conversely, when dismounting the sample container 1, the electromagnetic valve 8 is switched to allow the sample container to communicate with the open air. The single chip microcomputer 23 contains an A-D (analog-to-digital) converter for processing the analog signals input from the movable unit 10 and a timer counter portion for processing the pulse from the binarizing unit 15.

The operation of this disc cytometer is controlled with a software on an external PC. In other words, the PC issues commands to the disc cytometer, the commands are input into the single chip microcomputer 23 through the USB interface 25 and interpreted thereby.

In the following, the movable unit 10 will be described.

The movable unit 10 is for irradiating the sample container 1 with a laser beam and detecting the light scattered sideward and forward on laser irradiation. Thus, it consists of optical systems for laser irradiation and scattered light detection, which are integrally housed together.

The movable unit 10 includes: an XYZ axes controller 11 for moving the movable unit 10 in each axial direction X, Y and Z in 0.1 $\mu$m steps; an argon laser (wavelength of 488 nm) 12; a laser controller 13 for controlling the modes of argon laser 12 such as on-off and standby modes; a beam expander 26 for making up a confocal microscope optical system using the argon laser 12; a solenoid 16 for driving the beam expander 26; an object lens 27 for directing the laser beam from the argon laser 12 having passed through the beam expander 26 toward the sample container 1; a mirror 28 for bending the forward scattered light having passed through the sample container 1 through, for example, 90°; a condenser lens 29 provided on the light reflecting side of the mirror 28; a photomultiplier tube 18 provided on the light reflecting side of the condenser lens 29 for detecting the forward scattered light; a diaphragm unit 30 arranged between the condenser lens 29 and the photomultiplier tube 18; a solenoid 17 for driving the diaphragm unit 30; a condenser lens 31 for condensing the sideward scattered light from the sample container 1; a half-silvered mirror 32 arranged on the light reflecting side of the condenser lens 31; a photomultiplier tube 19 into which the light reflected by the half-silvered mirror 32 enters and which detects the intensity of the sideward scattered light; a diaphragm 35 provided between the half-silvered mirror 32 and the photomultiplier tube 19; a red-reflecting dichroic mirror 33 into which the light having passed through the half-silvered mirror enters; a photomultiplier tube 20 for detecting the red light reflected by the dichroic mirror 33; a diaphragm 36 arranged between the dichroic mirror 33 and the photomultiplier tube 20; a band pass filter 38 arranged between the diaphragm 36 and the photomultiplier tube 20; a green-reflecting dichroic mirror 34 into which the light having passed through the red-reflecting dichroic mirror 33 enters; a photomultiplier tube 21 for detecting the green light reflected by the dichroic mirror 34; a diaphragm 37 arranged between the dichroic mirror 34 and the photomultiplier tube 21; a band pass filter 39 arranged between the diaphragm 37 and the photomultiplier tube 21; and an amplifier 22 for amplifying the signals from the photomultiplier tubes 18 to 21 and outputting the amplified signals to the single chip microcomputer 23. In the movable unit 10, the XYZ axes controller 11, the laser controller 13, solenoids 16 and 17, and the amplifier 22 are controlled by the single chip microcomputer 23.

Next, the measurement by using the disc cytometer having the above-described constitution is described.

Figure 3:
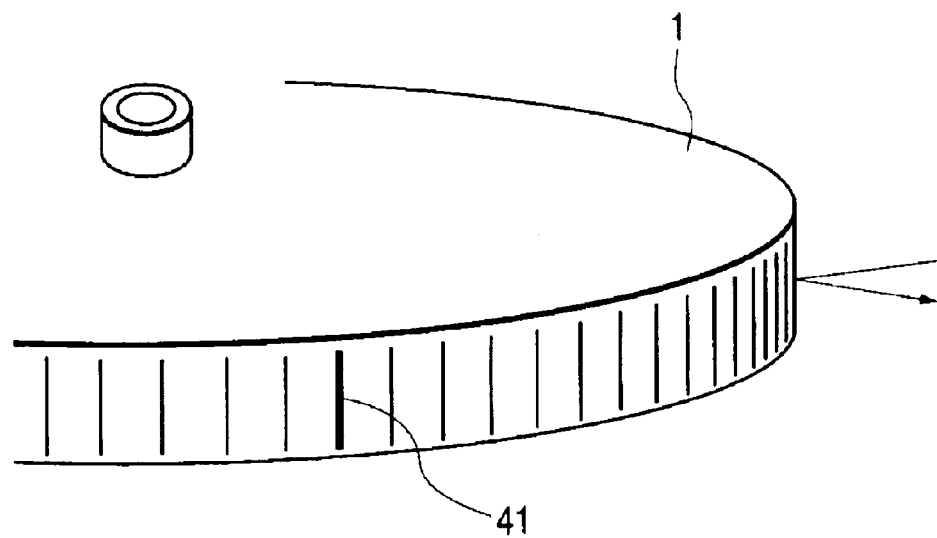
FIG. 3 is a view illustrating the structure for obtaining positional information of a sample container.

The sample container 1 mounted on the disc holder 5 is centrifuged with the motor 6 in accordance with the revolution, acceleration, deceleration and time provided to the motor controller 9 by the single chip microcomputer 23. After completing the centrifugation, a determination is carried out by irradiating the sample container 1 with the argon laser 12 while controlling the rotation speed of the sample container 1 in the tangential direction to be almost the same as that of the common flow cytometry, that is, 10 m/sec. At the time of making the determination, the radial position to be irradiated is controlled by the XYZ axes controller 11 in, for example, 0.1 $\mu$m steps. The revolution of the motor 6 at this point can be monitored with the reflection type sensor 14, directed toward the side surface of the sample container 1 and the binarizing unit 15 for binarizing the signals to introduce the encoder information, which is formed in the form of irregularities on the circumferential side surface of the sample container 1, to the timer counter portion of the single chip microcomputer 23. As shown in FIG. 3, a mark notch 41 having a different notch width is provided on the periphery of the sample container 1, and the absolute position of the sample container 1 is obtained by detecting the mark notch 41.

In the movable unit 10, after completing the centrifugation, the argon laser 12 is switched from the "standby" mode to the "on" mode by the laser controller 13. This allows the laser to start scanning the sample container 1. At this point, the beam expander 26 for making up the confocal microscope optical system is removed from the optical path by controlling the solenoid 16. The laser beam passes through the object lens 27, irradiates the sample container 1, and is split into the sideward scattered light scattered at 80° to the sample container 1 and the forward scattered light moving on straight. The forward scattered light having gone on straight is reflected by the mirror 28 and is condensed by the condenser lens 29. It then passes through the diaphragm unit 30 and enters into the photomultiplier tube 18. In the diaphragm unit 30, pinholes for making up the confocal optical system and the diaphragm for obtaining the scattered light scattered at 1 to 10° to the sample container 1 can be exchanged by operating the solenoid 17.

On the other hand, the sideward scattered light is introduced into three detectors (the photomultiplier tubes 19 to 21) after passing through the condenser lens 31. First, the sideward scattered light is split by the half-silvered mirror 32, and the reflected light is introduced into the photomultiplier tube 19, which is for determining the intensity of the sideward scattered light, via the diaphragm 35. On the other hand, the light that passed through the half-silvered mirror 32 is introduced into the red-reflecting dichroic mirror 33. The light reflected by the dichroic mirror 33 is introduced into the photomultiplier tube 20, which is for determining the intensity of red fluorescence, via the band pass filter 38 and the diaphragm 36. The light that passed through the red-reflecting dichroic mirror 33 is introduced into the photomultiplier tube 21, which is for determining the intensity of green fluorescence, by the green-reflecting dichroic mirror 34 via the band pass filter 39 and the diaphragm 37.

The light receiving signals from the photomultiplier tubes 18 to 21 are input into the A-D converting portion contained in the single chip microcomputer 23 from the amplifier 22 capable of controlling the gain of the photomultiplier tubes and are stored in the external memory 24 via a DMA (Direct Memory Access) controller of the single chip microcomputer 23.

For imaging, first, a confocal optical system is formed by operating the solenoids 16 and 17. Then, the origin is calculated from the mark notch 41 having a different notch width from the other notches on the periphery of the container 1. The position of the image to incorporate is calculated from the ring counter information that is reset to 0 after every round of the sample container 1 and the radial positional information. The laser irradiation is moved to the position. Then, an image is obtained by controlling the XYZ axes controller 11. Although a point-by-point scan is made in this embodiment because it adopts a confocal optical microscope system, it is also possible to use an optical system of a CCD (charge-coupled device) and a phase contrast microscope.

In the following, an actual experiment, where CD4 and CD8, lymphocyte surface antigens of human peripheral blood, were stained by using the device of the above embodiment, is described with experimental protocols.

Heparinized venous blood collected from a healthy subject was diluted 3-fold with PBS (phosphate-buffered saline). An 8 ml aliquot of the dilution was added to 2 ml of a Ficoll solution and centrifuged for 10 minutes at 1100 rpm. Then, the lymphocyte layer was removed with a pasteur pipette, washed with 10% FCS (Fetal Bovine Serum) in PBS twice, and adjusted to a lymphocyte concentration of $1 \times 10^7$ ml. Two milliliters of a 1:1 mixture of the FITC (fluorescein isothiocyanate)-labeled anti-CD4 monoclonal antibody and the PE (phycoerythrin)-labeled anti-CD8 monoclonal antibody were added to the above lymphocyte sample and the mixture was reacted at 4° C. for 30 minutes. After the reaction, the mixture was washed with 10% FCS-PBS three times to obtain a sample for the next step.

Figure 4:
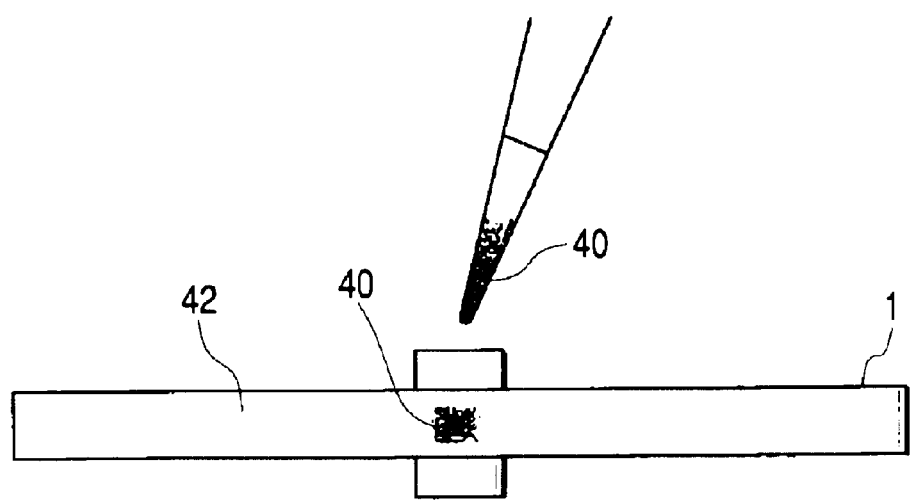
FIG. 4 is a view illustrating the positional relation in which a sample is disposed.
Figure 5:
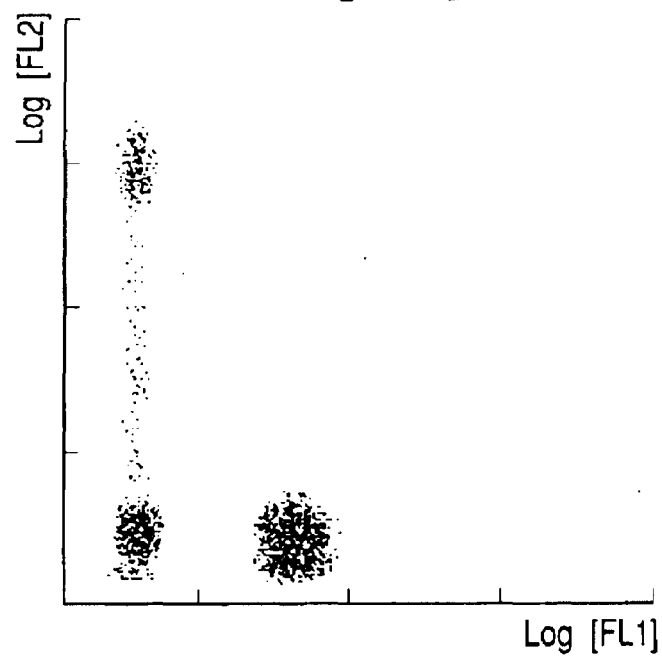
FIG. 5 is a graph showing an analytical result obtained.

The sample container 1 was filled with a Ficoll solution 42 in advance. Then, the sample 40 prepared as described above was injected into the center portion of the solution 42 (in other words, the center portion of the sample container 1) as shown in FIG. 4, and the container was mounted on the above-described disc cytometer to make a determination. The analytical results obtained with this experiment are shown in FIG. 5. In FIG. 5, both the ordinate and the abscissa are in a logarithmic scale, and the abscissa [FL1] represents the fluorescence intensity of FITC and the ordinate [FL2] the fluorescence intensity of PE.

Figure 6:
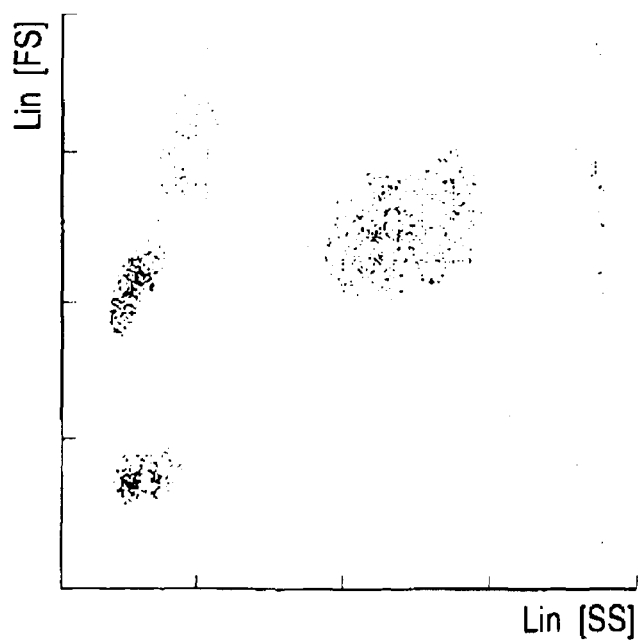
FIG. 6 is a graph showing an analytical result obtained.

The results obtained by changing parameters are plotted in FIG. 6. In FIG. 6, both the ordinate and the abscissa are linearly scaled. The abscissa [SS] represents the sideward scattered light intensity and the ordinate [FS] the forward scattered light intensity.

From the results shown in FIGS. 5 and 6, it was confirmed that the disc cytometer according to this invention has analytical functions equivalent to those of a current flow cytometer. Further, when a position where the strongest FITC fluorescence was observed in FIG. 5, thus a somewhat interesting position, was imaged by using a confocal laser microscope optical system, a peripherally stained image was a obtained. This confirms that the FITC-labeled anti-CD4 monoclonal antibody reacted with the surface antigen of a lymphocyte. In other words, staining was not a nonspecific staining, but corresponded to proper surface antigens.

As described above, the advantage of the present invention is that in addition to analytical results equivalent to those provided by the current flow cytometer, a sample preparation can be also obtained. Further, an advantage of the present invention is that it allows a more detailed analysis to be performed, because the actual stained image of cells, etc. selected under certain conditions can be repeatedly checked.

What is claimed is:

1. An analytical method comprising the steps of:
   preparing a sample containing a plurality of particulate substances;
   injecting the sample into a disc-shaped sample container;
   centrifuging the sample container to form a distribution of the particulate substances in the sample container; and
   carrying out an optical measurement on the sample container in which the distribution of the particulate substances has been formed, after said centrifuging step, to obtain at least one set of data selected from the group consisting of fluorescence intensity, scattered light intensity and a particle number of the particulate substances.

2. The analytical method according to claim 1, wherein the particulate substances are selected from the group consisting of cells, microbial cells, viruses, DNA and mitochondria.

3. The analytical method according to claim 1, wherein the optical measurement step includes a step of irradiating and scanning with a light beam on the sample container and detecting scattered light therefrom.

4. The analytical method according to claim 3, wherein the sample in the sample container is subjected to fluorescence-labeling of the particulate substances before centrifuging.

5. The analytical method according to claim 3, wherein image data on the particulate substances are obtained based on the analytical data.

6. An analytical device comprising:
   means for centrifuging a disc-shaped sample container;
   means for generating a light beam;
   means for scanning the sample container and irradiating a plurality of particulate substances having been centrifuged in the sample container with a light beam; and
   means for detecting scattered light from the sample container.

7. The analytical device according to claim 6, wherein the means for detecting scattered light is means for detecting a plurality of beams of light scattered from the particulate substances at different angles, and wherein fluorescence intensity and a number of the particulate substances are detected based on the detected beams of scattered light.

8. The analytical device according to claim 6, further comprising means for data processing and data analysis by A-D converting the detecting signals from the means for detecting scattered light and using the same as a parameter.

9. The analytical device according to claim 6, further comprising an optical system and image pick-up means for obtaining an image of the particulate substances.

10. The analytical device according to claim 6, wherein the particulate substances are selected from the group consisting of cells, microbial cells, viruses, DNA and mitochondria.

11. The analytical device according to claim 6, wherein the scanning and irradiating means scans the sample container being rotated with a laser beam in a radius direction.

* * * * *